(12) United States Patent
Nabet et al.

(10) Patent No.: US 8,120,014 B2
(45) Date of Patent: Feb. 21, 2012

(54) NANOWIRE BASED PLASMONICS

(75) Inventors: Bahram Nabet, Erdenheim, PA (US); Jonathan E. Spanier, Balacynwyd, PA (US)

(73) Assignee: Drexel University, Philadelphia, PA (US)

( * ) Notice: Subject to any disclaimer, the term of this patent is extended or adjusted under 35 U.S.C. 154(b) by 452 days.

(21) Appl. No.: 11/304,049

(22) Filed: Dec. 15, 2005

(65) Prior Publication Data

US 2006/0289761 A1 Dec. 28, 2006

Related U.S. Application Data

(60) Provisional application No. 60/636,259, filed on Dec. 15, 2004.

(51) Int. Cl.
*H01L 31/0352* (2006.01)
(52) U.S. Cl. ............ 257/21; 257/22; 257/184; 257/194; 257/E31.033; 257/429; 257/E31.038
(58) Field of Classification Search ................ 257/9–30; 385/1; 372/43–45
See application file for complete search history.

(56) References Cited

U.S. PATENT DOCUMENTS

| | | | |
|---|---|---|---|
| 5,777,390 A * | 7/1998 | Berger et al. ................ 257/749 |
| 6,624,017 B1 * | 9/2003 | Lombardo et al. ............ 438/235 |
| 6,773,616 B1 | 8/2004 | Chen |
| 6,819,845 B2 | 11/2004 | Lee |
| 6,882,051 B2 * | 4/2005 | Majumdar et al. ............ 257/746 |
| 6,996,147 B2 * | 2/2006 | Majumdar et al. ......... 372/43.01 |
| 7,064,372 B2 * | 6/2006 | Duan et al. .................... 257/296 |
| 7,254,151 B2 * | 8/2007 | Lieber et al. ................ 372/44.01 |
| 7,301,199 B2 * | 11/2007 | Lieber et al. .................. 257/327 |
| 7,342,441 B2 * | 3/2008 | Gorrell et al. ................ 329/346 |
| 7,489,870 B2 * | 2/2009 | Hillis et al. ................... 398/115 |
| 2004/0075464 A1 | 4/2004 | Samuelson |
| 2004/0136866 A1 | 7/2004 | Pontis |
| 2004/0188721 A1 | 9/2004 | Lieber |
| 2008/0009434 A1 * | 1/2008 | Reches et al. ..................... 514/2 |
| 2009/0266974 A1 * | 10/2009 | Verhulst et al. ............ 250/208.1 |

OTHER PUBLICATIONS

"Epitaxial core shell and core multi shell nanowire heterostructures" by Lieber et al.*
"Spectrum of 1D plasmons in a single stripe of 2D electrons" by Kukushkin et al.*
"Nonlinear carrier plasmon intercation in a 1D quantum plasma" by Bonitzs et al.*
"Sensing Thz signals with III-V Quantum nanostructures" by Hasegawa et al.*

(Continued)

*Primary Examiner* — Jerome Jackson, Jr.
(74) *Attorney, Agent, or Firm* — Knoble Yoshida & Dunleavy, LLC

(57) ABSTRACT

Nanoscaled, tunable detector devices for ultrasensitive detection of terahertz (THz) radiation based on the fabrication of one-dimensional (1D) plasma devices having clouds of strongly correlated and spatially confined electronic charge carriers are disclosed. These one-dimensional collective excitations ("plasmons") are realized using coaxial semiconducting core-shell nanowires or by electrostatically confining a two dimensional charge to one dimension. By exploiting the properties of plasmons confined to reduced dimensions and under a selected device configuration, conventional limitations on carrier drift and transit times that dictate the speed and sensitivity of transistors can be circumvented, and detector sensitivity can be improved. 1D devices with sub-picosecond response times will be important for a range of applications in diverse areas such as remote sensing and imaging, molecular spectroscopy, biotechnology, and in a range of the spectrum that has been difficult to detect. In addition to electromagnetic radiation these devices can be used as detectors of charged particle perturbations.

9 Claims, 8 Drawing Sheets

OTHER PUBLICATIONS

"Resonant detection of subThz and Thz radiation by plasma waves in submicron field effect transistors" by Knap et al.*

"Grating-bicoupled plasmon resonant Thz emitter fabricated with GaAs based heterostructure metamaterial systems" by Otsuji et al.*

"1D Plasmons in AlGaAs/GaAs quantum wires" by Demel et al.*

"Photonic bandgap effect in 1D plasma dielectric photonic crystals" by Mahto et al.*

"Epitaxial core-shell and core-multishell nanowire heterostructures" by Leiber etal.*

"Sensing THz signals with III-V Quantum nanostructures" by Hasegawa et al.*

"Photonic band gap effect in 1D plasma dielectric photonic crystals" by Mahto et al.*

Dyakonov et al IEEE Transactions on Electron Devices vol. 43 No. 10 Oct. 1996 pp. 1640-1645 "Plasma Wave Electronics: . . . Fluid".*

Michael I. Dyakonov et al., Plasma Wave Electronics: Novel Terahertz Devices Using Two Dimensional Electron Fluid, IEEE Transactions on Electron Devices, Oct. 1996, pp. 1640-1645, vol. 43, No. 10.

Michael S. Shur et al., Terahertz Sources and Detectors Using Two-dimensional Electronic Fluid in High Electron-Mobility Transistors, IEEE Transactions on Microwave Theory and Techniques, Apr. 2000, pp. 750-756, vol. 48, No. 4.

W. Knap et al., Resonant Detection of Subterahertz and Terahertz Radiation by Plasma Waves in Submicron Field-Effect Transistors, Applied Physics Letters, Dec. 2002, pp. 4637-4639, vol. 81, No. 24.

Martin Van Exter et al., Characterization of an Optoelectronic Terahertz Beam System, IEEE Transactions on Microwave Theory and Techniques, Nov. 1990, pp. 1684-1691, vol. 38, No. 11.

J. Kolodzey et al., The Design and Operation of TeraHertz Sources Based on Silicon Germanium Alloys, Paper Presented at the 2003 Topical Meeting on Silicon Monolithic Integrated Circuits in RF Systems, 2003, pp. 1-5.

Paul Harrison et al., Physical Model and Scattering Dynamics Engineering for Intersubband Lasers and Photodetectors, Conference on Optoelectronic and Microelectronic Materials and Devices, Dec. 2004, pp. 351-355, ISBN: 0-7803-8820-8.

Thomas W. Crowe et al., Opening the Terahertz Window with Integrated Diode Circuits, IEEE Journal of Solid-State Circuits, Oct. 2005, pp. 2104-2110, vol. 40, No. 10.

X. G. Peralta et al., THz Detection by Resonant 2-D Plasmons in Field Effect Devices, International Journal of High Speed Electronics and Systems, 2002, pp. 925-937, vol. 12, No. 3.

B. Nabet et al., Heterojunction and Heterodimensional Devices for Optoelectronics, IEEE Microwave Magazine, Mar. 2001, pp. 40-45.

Amro Anwar et al., Barrier Enhancement Mechanisms in Heterodimensional contacts and Their Effect on Current Transport, IEEE Transactions on Microwave Theory and Techniques, Jan. 2002, pp. 68-71, vol. 50, No. 1.

Xiying Chen et al., Resonant-Cavity-Enhanced Heterostructure Metal-Semiconductor-Metal Photodetector, Applied Physics Letters, Apr. 2002, pp. 3222-3224, vol. 80, No. 17.

Bahram Nabet et al., Photodetectors Based on Heterostructures for Opto-Electronic Applications, IEEE Transactions on Microwave Theory and Techniques, Oct. 2003, pp. 2063-2072, vol. 51, No. 10.

Bahram Nabet et al., On Optical Gain Mechanisms in a 2DEG Photodetector, Paper Presented at the 2001 Proceedings of the SMBO/IEEE MTT-S International Microwave and Optoelectronics Conference, 2003, pp. 57-60.

Xiying Chen et al., An AlGaAs-GaAs-Based RCE MSM Photodetector with Delta Modulation Doping, IEEE Electron Device Letters, May 2003, pp. 312-314, vol. 24, No. 5.

Gregory Tait et al., Physical Modeling of a Novel Barrier-Enhanced Quantum-Well Photodetector Device for Optical Receivers, Microwave and Optical Technology Letters, Feb. 2004, pp. 224-227, vol. 40, No. 3.

Gregory Tait et al., Current Transport Modeling in Quantum-Barrier-Enhanced Heterodimensional Contacts, IEEE Transactions on Electron Devices, Dec. 2003, pp. 2573-2578, vol. 50, No. 12.

Eric Gallo et al., Contact-Induced Properties of Semiconducting Nanowires and Their Local Gating, Guceri et al. Eds., Nato ASI Series, Nanoengineering and Nanofibrous Materials, Kluwer Academic Publishers, ISBN: 1-4020-2549-1, 2004, pp. 313-322.

* cited by examiner

- □ MSM
- ○ $S_{up}$-$S_{up}$
- △ $S_{down}$-$S_{down}$
- ▽ $O_{hmic}$-$O_{hmic}$ $6 \times 10^{17}$ cm$^{-3}$
- ◇ $O_{hmic}$-$O_{hmic}$ $3 \times 10^{17}$ cm$^{-3}$

NANOWIRE BASED PLASMONICS

CROSS-REFERENCE TO RELATED APPLICATIONS

This application claims the benefit under 35 U.S.C. §119(e) of U.S. Provisional Patent Application No. 60/636,259, filed on Dec. 15, 2004, the entire disclosure of which is hereby incorporated by reference as if set forth fully herein.

BACKGROUND OF THE INVENTION

1. Field of the Invention

The invention relates to the field of plasmonics. In particular the invention relates to detectors using one-dimensional confined charge in order to detect electromagnetic radiation and other perturbations such as charged particles.

2. Description of the Related Technology

It has long been recognized that reduced dimensionality and finite size play significant roles in the behavior of elementary excitations in solids. The effects of varying degrees of confinement of electrons, holes, excitons, phonons, polaritons, and magnons on the electrostatic, electronic transport, optical, dielectric, magnetic and thermal properties of solids have been areas of sustained, yet intense, investigation for several decades.

Among these elementary excitations in solids are plasmons, which are oscillations in charge density relative to the background (charges) of screened impurities. A plasmon is the particle resulting from the quantization of plasma oscillations, which are density waves of the charge carriers in a conducting medium such as a metal, semiconductor, or plasma. Of both scientific interest and technological application have been surface plasmons in metal nanostructures for resonant detection and identification of individual molecules based on local enhancements ($\sim10^4$) of electromagnetic fields using, for example, inelastic light scattering. Of crucial importance to several generations of solid-state semiconducting devices is the altered behavior of electrons and holes when electrostatically confined within one or more planes. When carriers exist in sufficiently high concentrations and/or are in sufficiently excited states, their oscillations are quantized as plasmons, obeying Bose-Einstein statistics. Plasmons in a two-dimensional electron state were first reported and observed in liquid He in 1976, and later in inversion layers of Si in 1977 and GaAs in 1979.

Quasi-one-dimensional structures consisting of electrostatically or compositionally confined strips within epitaxial quantum wells (vicinal growth) first appeared and were investigated more than two decades ago. In 1998, controlled growth of single-crystalline Si nanowires using laser-catalyzed vapor-liquid-solid techniques was first accomplished ushering in a new platform for one-dimensional materials and devices. In subsequent work reported primarily by investigators in the group of Charles M. Lieber at Harvard, syntheses of a range of elemental and binary semiconductor nanowire compositions with control of diameter using metal nanocluster catalyst particles were reported. Significantly, the tremendous utility of the nanowire platform was further advanced in 2002 when Gudiksen and Lauhon, et al. demonstrated axial modulation of composition and dopant in the GaAs and GaP family to form superlattices within individual nanowires. Equally significant was the demonstration, soon after, by Lauhon and Gudiksen, et al. of co-axial nanowires consisting of Si cores on which multiple epitaxial shells composed of Ge and Si were grown. In these works, the authors also fabricated and characterized heterojunction diodes, LEDs and FET devices with these new nanowire and device geometries, and measured the optical response thereof.

Devices based on plasmon action may have an impact on sensing comparable to what the discovery of transistor action had on electronics, that is, while the risks of crafting a dense plasma in a solid in nanoscale is high, its pay-off is proportionally high. Detection of the terahertz (THz) range of the electromagnetic spectrum, as well as other ranges of the electromagnetic spectrum, can play an important role in a variety of different technological and commercial fields.

Typical THz components fall into two categories: sources and detectors. Other components such as waveguides, filters, antennas, amplifiers, and THz materials are also important to THz technology. Terahertz sources are difficult components to realize. The reasons include the high frequency roll-off of the electronic solid-state sources due to the reactive parasitics, difficulties that tubes face because of metallic losses and scaling problems, and low level photon energies (meV) of solid-state lasers operating at this range, where the energy is comparable to the relaxation energy of the crystal. As far as power level is concerned, the frequency conversion techniques, either up from a millimeter wave, or down from the optical and IR range, have been the most successful techniques.

One of the components that has received a lot of attention is the diode frequency multiplier. Varactor diode and Schottky diode multiplier circuits have been introduced for multiplying MMW signals up to a few hundred GHz. Recently, a 200 to 2700 GHz multistage frequency multiplier was introduced using Schottky diodes on an extremely thin GaAs substrate and was developed as a source. A sub-millimeter-wave sideband generator consisting of a whisker contacted Schottky varactor mounted in a waveguide was another recently developed source. Some other methods of THz generation as reported by Kolodzey et al. are quantum well intersubband transition in SiGe, boron doped resonant state transition in strained SiGe, and impurity transitions in doped Si.

A unique feature of THz frequencies compared to shorter wavelengths is that the ambient background thermal noise almost always dominates the naturally emitted narrowband signals. Therefore, either cryogenic cooling or long integration time radiometric techniques, or both, are typically required. Currently, there are no existing methods for detecting THz radiation at room temperature. Using the instant invention's nanowire plasma devices as high-speed, room temperature THz detectors can overcome these drawbacks in the prior art. Furthermore, utilization of one dimensional nanowire technology can also serve a role in providing fast and reliable detectors of other ranges of electromagnetic radiation.

Confinement of elementary excitations in one or more dimensions has enabled the development of numerous and important advances in electronic and photonic devices. Controlled variation of the energy level spacing and availability of electronic states using geometric or electrostatic confinement of carriers in quantum wells, quantum wires and quantum dots has led to important advances in transistors, diodes, LEDS, photodetectors and LASERS. Experimental realization of systems in which carriers are effectively confined within planes, along one-dimension, in current rings, or through narrow constrictions or islands, have attracted enormous interest. Detailed investigations in mesoscopic systems have uncovered a range of exciting and unique electronic transport properties, including electron cavities, Kondo physics, the Aharonov-Bohm effect, and other effects, including quantum cascade LASERS, phonon confinement; optical phonon, and exciton confinement.

The current state-of-the-art with respect to high speed transistor technology relies on modulation doping of heterostructures, allowing carriers to be effectively screened from dopant ions, and thus their travel to be subject only to lattice and external forces. These high electron mobility transistors (HEMTS) are characterized by a high-density two dimensional electron (hole) gas (n, p~$10^{12}$ cm$^{-3}$) and a heterojunction that exists between wide and narrow band-gap materials. Doping of the wide band-gap material introduces carriers that are transferred to the narrow band-gap material, and confined due to the band-gap discontinuity. The two-dimensional electron gas (2DEG) or hole gas (2DHG), under appropriate gating, constitute the conduction channels for n-type and p-type HEMT devices. In a HEMT device, gating of this channel of charge produces a transistor action and the speed of the device is limited by the transit time of the carriers from source to drain. The model is that of a reservoir-channel-reservoir with the channel consisting of the 2DEG (or 2DEHG), and the reservoirs of electrons being ohmic metals of the source and the drain. Transit of electrons in this 2DEG (2DHG) is expedited since scattering by ionized dopants is removed; the conduction of the channel remains bounded by the electric-field dependent drift velocity of electrons, or holes. However, a different mechanism of charge, or energy, transport exists when a reservoir of carriers is sandwiched between two barriers: here a carrier density wave, similar to a wave in a pond, propagates and is subject to different constraints. When spatially confined, these electron density waves become quantized forming plasmons. These plasmons can be produced for ultra sensitive detection of external perturbation.

Therefore, there exists a need for applying plasmon-based devices to improve sensing of terahertz radiation and other electromagnetic radiation in order to provide viable, highly sensitive, detectors.

SUMMARY OF THE INVENTION

Accordingly, it is an object of certain embodiments of the invention to provide plasmon-based device that employs one-dimensional plasma technology to sense electromagnetic radiation.

One aspect of the invention relates to a detector for detecting electromagnetic radiation having an inner material, an outer material surrounding the inner material, a one-dimensional plasma confined in the detector, and Schottky contacts associated with at least one of the inner and outer materials.

A second aspect of the invention is a method for making a detector for detecting electromagnetic radiation including the steps of forming a one-dimensional plasma; and detecting plasmons caused by perturbations of the one-dimensional plasma by at least one of the group consisting of electromagnetic radiation and charged particles.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 3b shows a close up view of the AlGaAs material shown in FIG. 3a.

DETAILED DESCRIPTION OF THE PREFERRED EMBODIMENT(S)

Figure 1A:
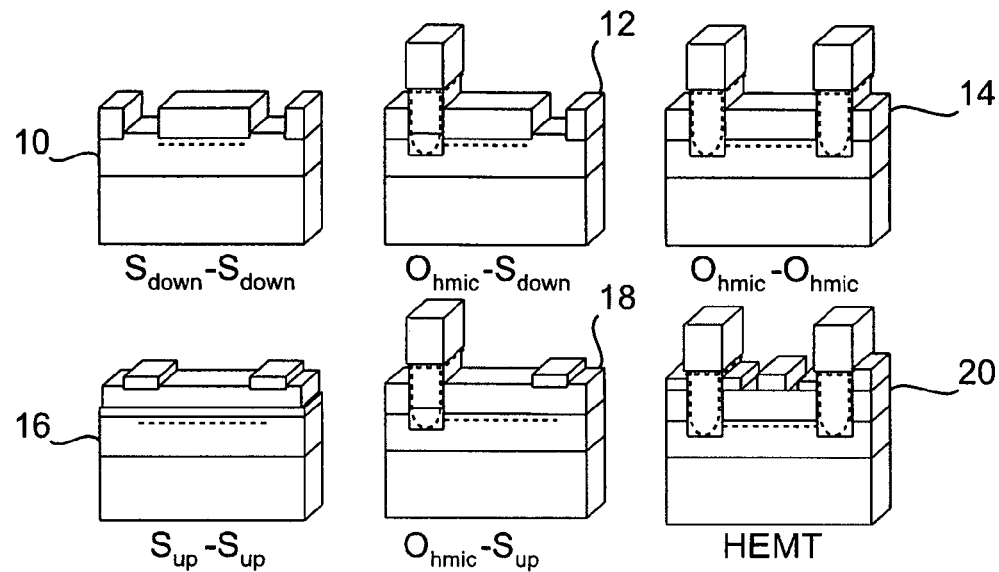
FIG. 1A shows schematic representations of a series of comparative devices based on two-dimensional electron gas or plasma.

An electron, or hole plasma is a cloud of strongly interacting electrons, or holes within a region, layer, filament or other volume of a solid. It is accomplished by providing sufficient levels of doping by donors, or acceptors in an adjacent region. In both cases, the plasma is distinguished by the collective behavior of the charge carriers by either collectively carrying negative or positive charge. Among elementary excitations in solids with relatively high carrier concentration are plasmons. Plasmons are collective, quantized oscillations of a free electron, or hole, gas relative to the positively (negatively) charged background of ionized donors, or acceptors. This property is best elicited when the mobile charge carriers are spatially separated from donors and acceptors by, for example, modulation doping of a heterostructure. These excitations are important for understanding the optical properties and dielectric response of metals, since plasma frequencies in metals are typically in the visible or ultraviolet range. In particular, it has long been recognized that at nanostructured surfaces, plasmons produce significant enhancements of the local electric field intensities in response to electromagnetic radiation. These resonant enhancements are the basis for ultra-high-sensitivity detection of physisorbed or chemisorbed, molecular analytes using surface plasmon resonance (SPR) and surface enhanced Raman scattering (SERS) techniques. In semiconductors, however, the plasma frequencies are typically in the near infrared range (NIR). In fact, gated field effect transistors (FETs) have been used as tunable resonant detectors of terahertz radiation by plasmons confined to two dimensions, exploiting the fact that the velocity of the plasmons (~$10^8$ cm/s) far exceeds the drift velocity in the two-dimensional electrons in the FET channel.

Perturbation of this plasma by external stimulus, be it THz radiation, optical radiation, or charged particles, results in a collective interaction, the rate of which is based on fundamental carrier-collective carrier or plasmon scattering rate, which is on the order of a picoseconds. Indeed, thermalization time, the time at which a cloud of carriers reaches a new thermal equilibrium distribution, is reported to be as short as 10 femtoseconds for electrons and 60 femtoseconds for holes. Thus, insofar as such a cloud of charge can be maintained in quasi equilibrium, it reacts to external stimulus with sub-picosecond time constants. Such capability does not exist in a conduction channel of a transistor due to the flow of current.

Thus, though modulation doping is an important feature of the devices, the subject matter of the instant invention differs from previous work in one or more of the following ways:

(1) Electrical contact with the one-dimensional device is achieved via blocking Schottky contacts, as opposed to Ohmic contacts; this enables an electron gas to be maintained as a reservoir of nearly free carriers under quasi equilibrium, and leads to many orders of magnitude improvement in the sensitivity, responsiveness and speed of detectors based on this scenario.

(2) The dimensionality of the carrier plasma is reduced to geometrically confined, tunable, one-dimensional device structures; these one-dimensional device structures achieve new levels of high performance for device design and for platform/substrate flexibility and integration. The nanowire geometry and proposed one-dimensional device structures also permit systematic experimental investigation of plasmons in shell-like geometries. A dense filament of charge encapsulated in nano scale dimensions and designed to elicit a resonant response to perturbation is produced. These natural resonant frequencies are tuned by controlling carrier density by doping or by gating.

(3) The platform for these one-dimensional devices permits novel design variables for tunability that allow for resonant detection of THz radiation; in addition to the device or cavity length that determines the natural plasmon frequencies, spatial modulation of the band-gap is introduced, and alternatively, spatial modulation of the carrier concentration in components of the device structure, resulting in controlled spatial variation of the charge density, i.e. the plasmons. Moreover, these strategies enable the design of nanowire plasmon filters that permit sensing of radiation over a selected band.

The one-dimensional confined charge can be created by a bottom-up approach using nanowire technology, or with a top-down approach of electrostatically confining a two dimensional electron, or hole, gas.

The proposed nanowire technology permits development of applications such as tunable room temperature detection of THz radiation. "Room temperature" is taken to typically be roughly 21-23° Celsius (68-72° Fahrenheit), or 294-296 kelvin (K). The "standard" room temperature is 22° C. (72° F.), or 295 K. However, it should be noted that room temperature for the purposes of the one-dimensional device can be construed to include from 2-36° C., 35.6-96.8° F., or 275-309 K.

Plasmon frequencies can be designed to fall within the terahertz region of the electromagnetic spectrum. Terahertz (THz) is broadly applicable to sub-millimeter-wave energy that covers the wavelength range between 1000-100 µm (300 GHz-3 THz), corresponding to the approximate photon energy between 1.2-12.4 meV and an equivalent blackbody temperature of 14-140 K. For years the applications of THz techniques have been limited to research labs and institutions, and this range has been one of the least used of electromagnetic spectrum. However, the commercial uses of terahertz technology are promising.

The advantages of the terahertz time domain technique, as well as the availability of semiconductor-diode-pumped solid-state lasers and advances in terahertz transmitters and receivers, have led to real-time imaging in the terahertz domain called T-Ray imaging. T-ray imaging technology combines imaging, real time acquisition of terahertz waveforms and advanced signal processing to obtain far-infrared images of objects and materials. T-Rays are able to be used for research applications, such as plasma fusion diagnostics, electron bunch diagnostics, mapping of current distribution in electronic devices, and THz spintronics; commercial applications such as, skin imaging for cancer detection, mail inspection, luggage inspection, and gas spectroscopy; and defense applications such as, homeland security, chemical and biological agent detection, explosives detection, see-through-the-wall technology, and imaging in space using satellites.

Terahertz technology is also useful for the molecular spectroscopy of the earth, planets, and space. Many key species either have thermal emission line peaks or their first rotational or vibrational line emissions in the sub-millimeter range, especially between 300-2500 GHz, and are best observed from platforms above the Earth's atmosphere.

Figure 1B:
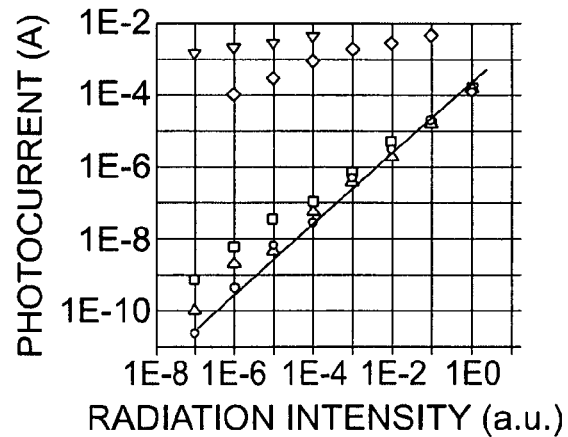
FIG. 1B shows a graph of DC current as a function of light intensity for several of the devices of FIG. 1A.

A family of photodetector devices, shown in FIG. 1A, was developed that took advantage of electron confinement to achieve reduced noise, high speed, and high sensitivity. The device family is shown schematically in the top portion of FIG. 1A. Shown in the device family are Schottky contacts down device 10, Ohmic-Schottky down device 12, ohmic contact device 14, Schottky contacts device 16, Ohmic-Schottky up device 18, and a high electron mobility transistor (HEMT) 20. All devices, including HEMT 20, work on the basis of the properties of a two-dimensional electron gas (2DEG) that is formed due to the layered heterojunction. Different types of contacts to this 2DEG gas differentiate the devices. FIG. 1B is a graph depicting the response of these devices in the dark and under various light intensities. Large differences (~$10^6$) are observed based on the contact type. That is, the Schottky contacts device 16 conducts less than 10 picoamps in darkness, while the ohmic contact device 14 conducts 8 orders of magnitude more current under darkness. The behavior of these devices demonstrates that a device with blocking contacts is in quasi-equilibrium while the typical FET device is not. It is further noted that the channel charge density in both devices is the same and quite large while current flow is different by many orders of magnitude.

Figure 2:
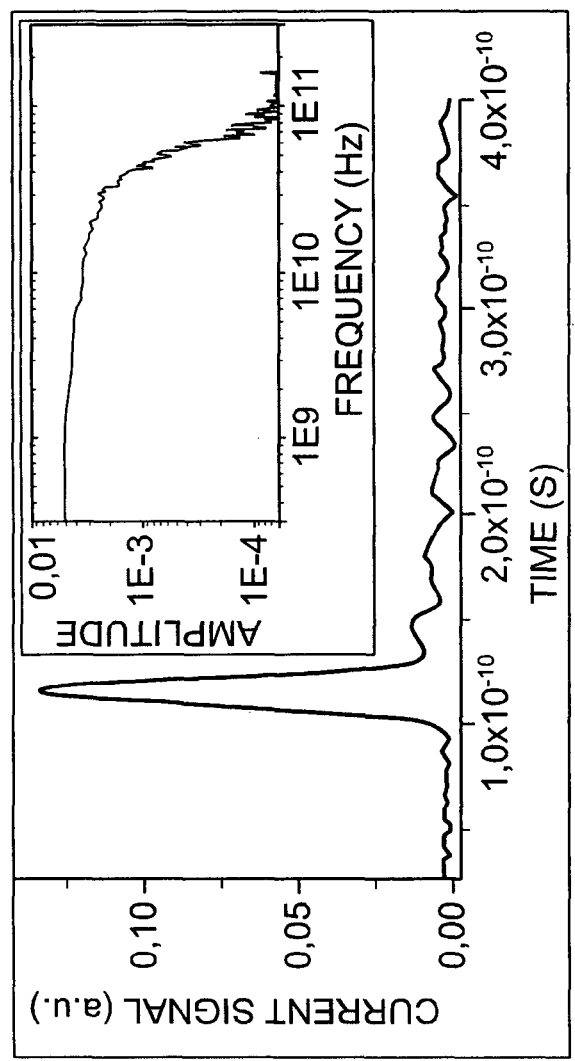
FIG. 2 shows a graph depicting the response of a barrier enhanced, two-dimensional electron gas based photodetector such as are depicted in FIG. 1 to excitation be a femtosecond Ti:Sapphire laser pulse and, in the inset, the Fourier Transform of the trace.

These devices have shown a good range of sensitivity; up to eight orders of magnitude dynamic range is observed as a function of intensity in FIG. 1B. In addition, these devices exhibited a very high speed of response, as shown in FIG. 2 where a graph depicting response to a femtosecond Ti:Sapphire laser pulse and its Fourier Transform (inset) are shown, demonstrating the ability of a large area device to operate in tens of GHz. FIG. 2 shows the response of a barrier enhanced 2DEG based photodetector to excitation by a femtosecond laser pulse. The inset shows the Fourier Transform of the trace. Short traces showed fall time and FWHM values below 9 picoseconds. Such a combination of high speed, high responsiveness, and high sensitivity is obtained by forcing the devices to operate in a reduced dimensional regime, but as shown below cannot be expected from transit of optically generated carriers.

Figure 4A:
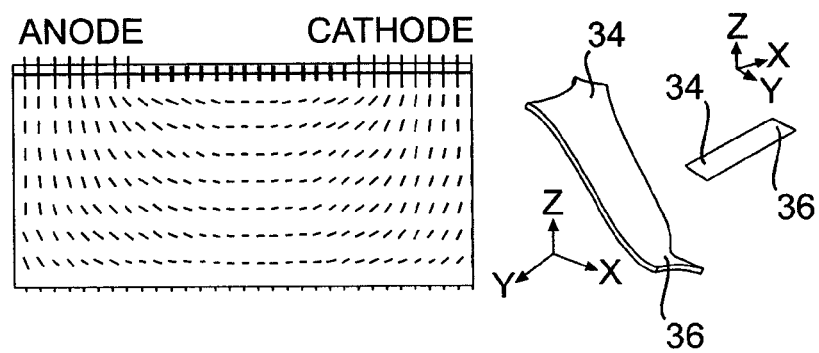
FIGS. 4a-4b show a comparison of the effect of doping of a semiconductor layer on carrier density, energy band and electric field.
Figure 4B:
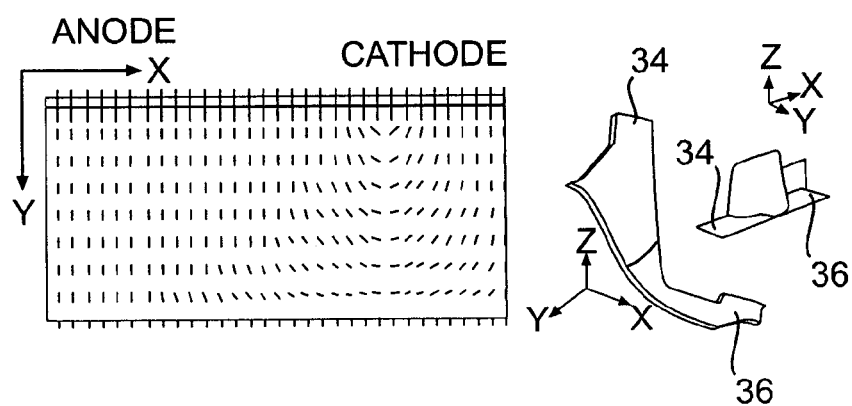

Analysis of the devices shown in FIG. 1A demonstrates that the devices have shown speeds higher than typically permitted by the transit time (i.e., sweep out) of the optically generated carriers. That is the devices have been tested with a contact separation of 4 μm, which showed the speed of a sub-micrometer device. Detailed simulation of the electric field, potential, and carrier concentration, as well as dynamics of carrier transport has been conducted as shown in FIGS. 4a-4b. FIGS. 4a-4b show a comparison of the effect of doping on the carrier density, energy band and electric field. The devices depicted in FIGS. 4a-4b each include a cathode 34 and an anode 36. The top left of FIG. 4a shows the electric field's lateral orientation in an undoped device. The conduction band and carrier concentration are shown in the upper right of FIG. 4a. The bottom left of FIG. 4b shows the vertical orientation of an electric field in a doped device and the bottom right of FIG. 4b shows the energy band diagram and high density of carriers. Comparison of carrier density profiles shows the expected high density of mobile carriers when the widegap is doped. Consistent with this reservoir of charge is band bending that is quite different for the doped device, by showing the characteristic of a plasma when changes occur at the cathode within a small Debye length, while gradual changes in potential are observed for an undoped device. The orientation of the electric field is also significantly altered due to the 2DEG. Experimental and simulation results show that the electron cloud collectively responds to external perturbation with time constants that are much faster than the transit times. Hence, an optically generated electron that arrives in the 2DEG need not travel to the contacts to be collected; the relaxation of the cloud causes current to flow in the external circuitry with a time constant of the order of the dielectric relaxation time, that is, less than a picosecond.

Figure 3A:
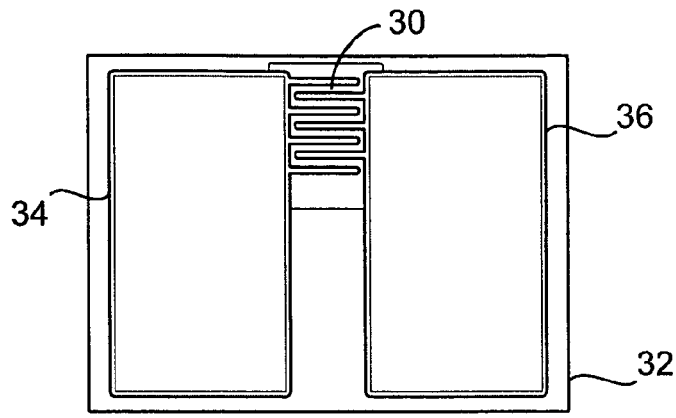
FIG. 3a shows a top down view of a two-dimensional electron gas device.
Figure 3B:
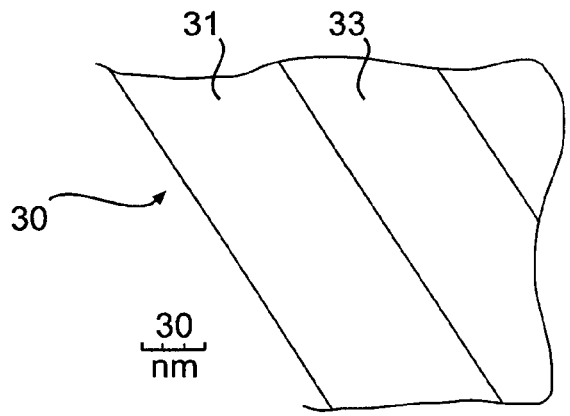
Figure 3C:
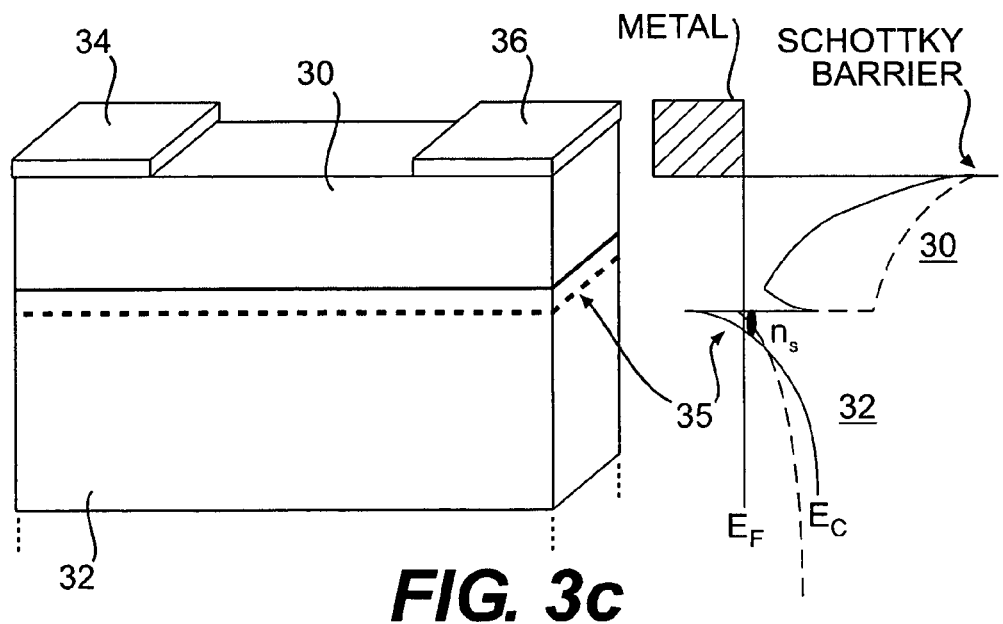
FIG. 3c shows a schematic diagram of a heterojunction metal-semiconductor-metal photodetector with Schottky contacts.

In order to fully understand the one-dimensional nanowire devices, it is helpful to view the basic system first in terms of the two dimensional system as it is shown in FIG. 3a-3c. FIG. 3a shows a top down view of a two-dimensional device showing cathode 34 which is a gold pad, an anode 36 which is a gold pad, the undoped GaAs layer 32, and the AlGaAs layer 30. FIG. 3b shows a close up view of AlGaAs material 30 including $Al_{0.9}GaAs$ layer 31 and $Al_{0.24}GaAs$ layer 33. FIG. 3c shows a schematic diagram of a heterojunction metal-semiconductor-metal photodetector with Schottky contacts. The undoped GaAs layer 32 has a thickness of 1175 Å in FIG. 3c. The AlGaAs layer of FIG. 3c has Al=0.24 and a thickness of 50+500 Å. The energy band diagram is shown at the right when the widegap material is doped (solid line) or undoped (dashed line). Similar to a high electron mobility transistor (HEMT), doping of an AlGaAs/GaAs heterostructure produces a two-dimensional electron gas (2-DEG) 35 at the heterointerface on the narrow gap side. This 2DEG 35 is confined in a triangular potential well that is formed on one side due to conduction band discontinuity and the other side due to band banding. An internal electric field is formed due to charge transfer across the heterointerface that confines the resultant transferred charge. While in the HEMT device, the 2DEG 35 is contacted by the ohmic source and drain metal through a deep annealing process, in this device two Schottky contacts 34 are made on top of the AlGaAs layer 30. These are a variation of Metal-Semiconductor-Metal (MSM) Photodetector devices where current transport under darkness is primarily determined by thermionic emission of carriers across the Metal-widegap semiconductor. The existence of the 2DEG 35 is shown to affect this transport of charge partially because of the reduced dimensional nature of the density of states in the semiconductor and partially due to the Coulombic force that this cloud of charge exerts on the emitted carriers from metal. The effect of this force appears as an increase in barrier height, and hence decreases the thermionic emission current. A device with a channel having a large number of free electrons shows less dark current than one without such a reservoir of mobile carriers. These new devices demand controlled growth of one-dimensional nanostructures.

Figure 5A:
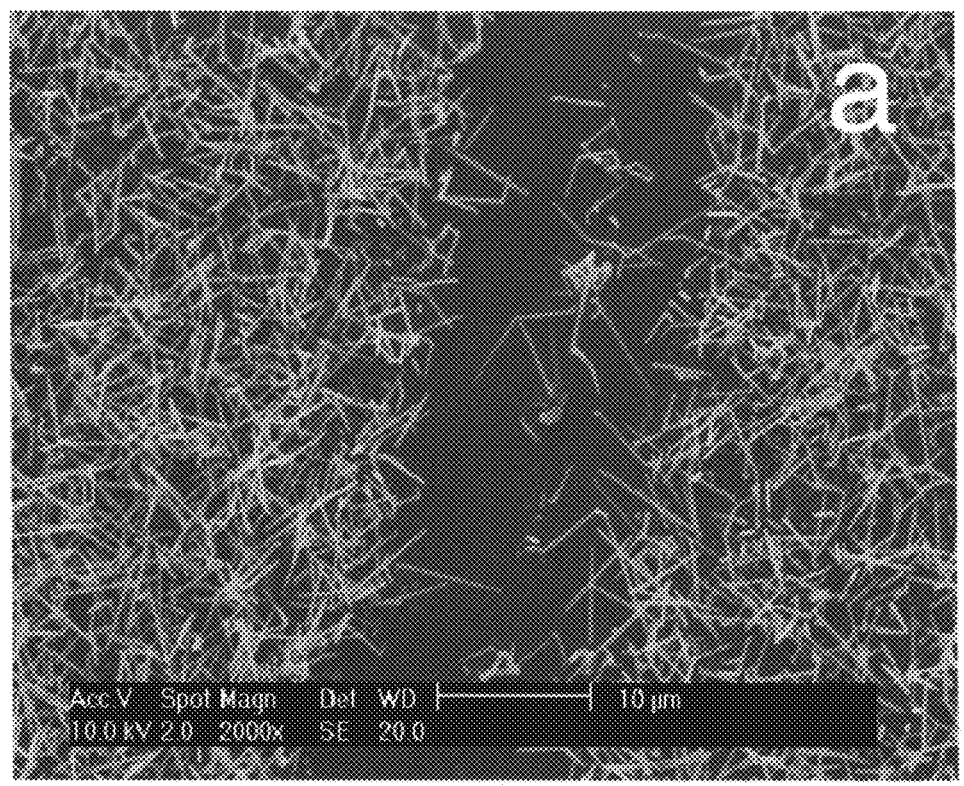
FIG. 5a shows an example of nanowire.
Figure 5B:
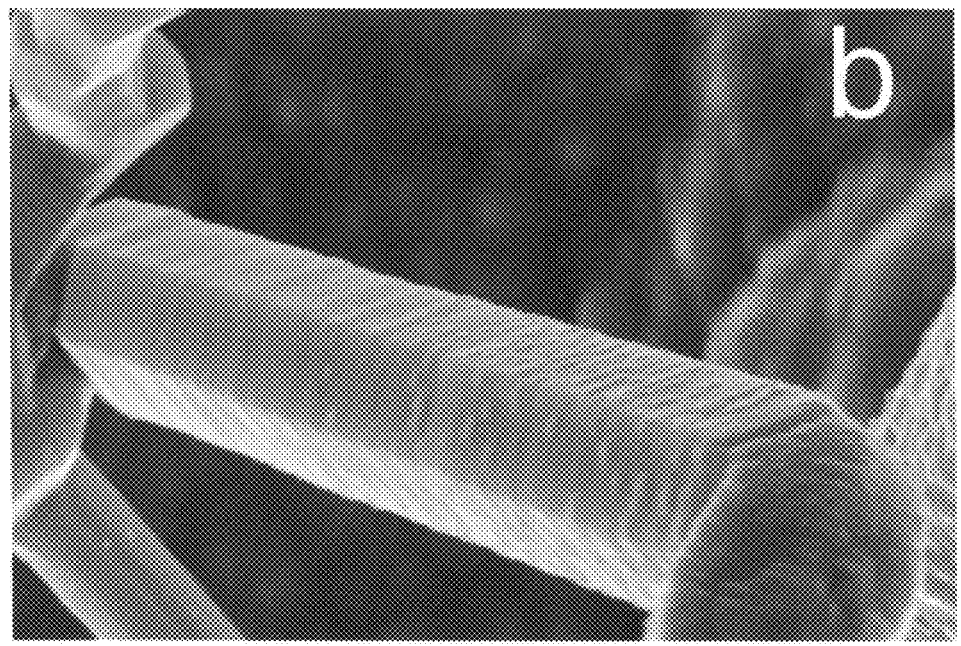
FIG. 5b shows hexagonal-faceted Si nanowires.

A chemical vapor deposition device has been assembled that has the capability of growing one-dimensional devices, such as Group IV (Si, Ge and $Si_xGe_{1-x}$) nanowires and core-shell nanowires using vapor-liquid-solid and related methods, and also a system that has the capability to grow III-V nanowires in a separate, dedicated system. The growth conditions in the system produce a high yield of single-crystalline nanowires on a metal colloid with control of diameter and length. A representative example of the nanowire yield is shown in FIG. 5a. The conditions for reproducibly growing new types of Si nanostructures, such as strongly tapered Si nanostructured polyhedra, essentially nanocones with facets, and hexagonal, faceted Si nanowires, shown in FIG. 5b, have been identified. These new types of Si nanostructures are grown using a combination of controlled variables during synthesis, including, but not limited to the selection of a range of vacuum pressure and its controlled variation with time (50-500 torr); high silane partial pressures; substrate and catalyst preparation and placement; and creation of high energy surfaces/nucleation sites. These nanostructured topologies offer the possibility of probing the effects of dimensionality on the plasmons and plasmonic devices within individual nanostructures: the large ends of these are hundreds of nanometers in diameter, while the narrow tips have radii of curvature of 1-2 nm.

The above results demonstrate how the collective response of a 2DEG can be used to overcome transit time limitations of a photodetector device, thus allowing access to much smaller relaxation time constants for detection of high-speed phenomena. Importantly, the collective excitation spectrum in one-dimensional systems is markedly different from that for two- and three-dimensional systems, and has significant ramifications for the design and enhanced performance of the one-dimensional devices. Below are summarized the theoretically derived results of the dispersion characteristics of plasmons in three, two and one dimensions. For simplicity electron plasmas are used in the discussion below, however it is to be understood that these results apply to hole plasmas as well.

Electrons confined to two or one dimensions are characterized by wave functions and eigenvalues that depend upon dimensionality, the shape of the confining potential (e.g. it is a square well or parabolic), the geometry and size of the cross-section. The strength of confinement and resulting behavior may be material specific (e.g. driven by the relative size of the confined structure and one or more relevant length scales, such as the Fermi wavelength, or Bohr excitonic radius). The population of the electronic levels, and the conditions under which either diffusive or ballistic transport prevails are important considerations in quantum systems, but are not central to the present discussion, since the instant invention focuses on the collective properties of one-dimensional electronic systems, and how these can be exploited for the sensing of perturbations of these systems on a timescale that is not limited by the drift velocity.

3D Electron Plasma

The plasma frequency for 3D systems can be obtained analytically simply by solving the equation of motion of the electrons oscillating with respect to the background of ionized donors, $$\omega_p \left( \frac{n_{3D} e^2}{\varepsilon m_e} \right)^{1/2},$$

where $n_{3D}$ is the electron density and $m_e$ the effective mass of electrons. Further insight into the behavior of these systems, including the dispersion and the effects of reduced dimensionality, have been obtained by using the Lindhard dielectric function, or random phase approximation (RPA), in which the dielectric function is expressed in terms of an effective Coulomb potential and an electron density-density correlation function. The dispersion of the plasmon can be approximated as $$\omega = \omega_p \left( 1 + \frac{3}{10} \frac{q^2 v_F^2}{\omega_p} + \ldots \right)$$

where $v_F = \nabla k_F/m$ and $k_F = (3n_{3D}\pi^2)^{1/3}$. The dispersion of the plasmons in 3D systems is characterized by a frequency $\omega_p$ at $q=0$, and a nearly flat dispersion for increasing q until the plasmon line crosses the region of the excitons, corresponding to scattering into single-particle excitations. Two key features are that (a) the nonzero value of $\omega_p$ at $q=0$ dictates that only electromagnetic radiation with $\omega \tau \omega_p$ can excite the plasmon, and (b) the frequency region over which the plasmons are long-lived and do not decay is rather narrow.

2D Electron Plasma

For 2D electron systems, the plasmon dispersion is:

$$\omega = \left( \frac{n_{2D} e^2}{2\varepsilon m} q_\parallel \right)^{1/2}$$

In which a more accurate expression for a real case of a silicon MOS or a GaAs/AlGaAs heterojunction structure can be obtained by replacing $\in$ with $\in_{NG} + \in_{WG} \coth(q_{s1} d)$, where $\in_{NG}$ and $\in_{WG}$ are the dielectric functions of the oxide (AlGaAs) and silicon (GaAs) layers, and d is the thickness of the oxide (AlGaAs) layer. Here the plasmon dispersion also starts at $\omega=0$ for $q=0$, but the frequency region of long-lived plasmons is wider than that for 3D, but also scatters into excitons for larger values of q.

1D Electron Plasma

Finally for the 1D system, the dispersion also starts at zero frequency, but with $$\omega = \omega_0 q_z a \left| -\ln\left(\frac{q_z a}{2}\right) \right|^{1/2} + O(q_z^2), \text{ and}$$

$$\omega_0 = \left( \frac{2n_{1D} e^2}{\varepsilon m a^2} \right)^{1/2}.$$

Significantly, in the Random Phase Approximation (RPA) of the 1D system, the plasmon mode dispersion does not intersect the exciton spectrum and therefore does not scatter and dissipate. It is noted that the dispersion for 2D is sub-linear ($\sim q^{1/2}$), unlike that for 1D, which is essentially linear, as also confirmed by resonant inelastic light scattering.

The instant invention creates tunable detectors of THz radiation. The devices are optimized by adjusting the carrier concentration, and by selecting a geometric device length of L, since the values of the plasma frequency are discretized according to $\omega_N = \omega_L(1+2N)$, where here $\omega_L \pi v_p/2L$ and $v_n$ is given by $d\omega/dq_z$ above. The contacts can be considered to be reflectors of the electron wave; hence better cavity/plasmon modes are expected since the gate should change the charge only. This device acts similar to the gated FETs.

Other factors come into play, including distinctions between intra- and inter-subband plasmons, and scattering from screened and unscreened impurities. The effects of scattering from interfaces (and surfaces, where applicable) and their associated roughness, as well as scattering by longitudinal optical (LO) phonons at finite temperatures limit the relaxation time and thus the effective mobility of the system. Nevertheless, a strong need exists for using the unique response of 1D plasmons in devices such as tunable photodetectors and THz detectors in which the response time to a perturbation and effective transit time for the collection of carriers is related to the group velocity of the plasma and not the scattering-limited drift velocity of the carriers.

Core-shell co-axial nanowires composed of GaAs/AlGaAs, of Ge/SiGe/Si and of SiGe/SiO$_2$/metal architectures are grown in order to create the 1D devices. The growths are carried out using chemical vapor deposition of gaseous precursors (e.g. SiH$_4$, GeH$_4$, PH$_3$ and B$_2$H$_6$) in mixtures of Ar, N$_2$ and H$_2$ carrier gas at low vacuum pressures (~1-500 torr) using metal nanocluster-catalyzed vapor-liquid-solid methods. Following the growth of nanowire cores, the growth conditions (temperature, pressure, position in furnace) favor predominantly radial, surface growth that enables the formation of co-axial architectures.

Modulation-doped heterojunction devices are fabricated in configurations involving co-axial nanowires composed of material systems that have been previously studied in 2D systems—namely GaAs/AlGaAs and Ge/SiGe/Si. Schematic diagrams of these devices are shown in FIGS. 6a and 6b.

Figure 6A:
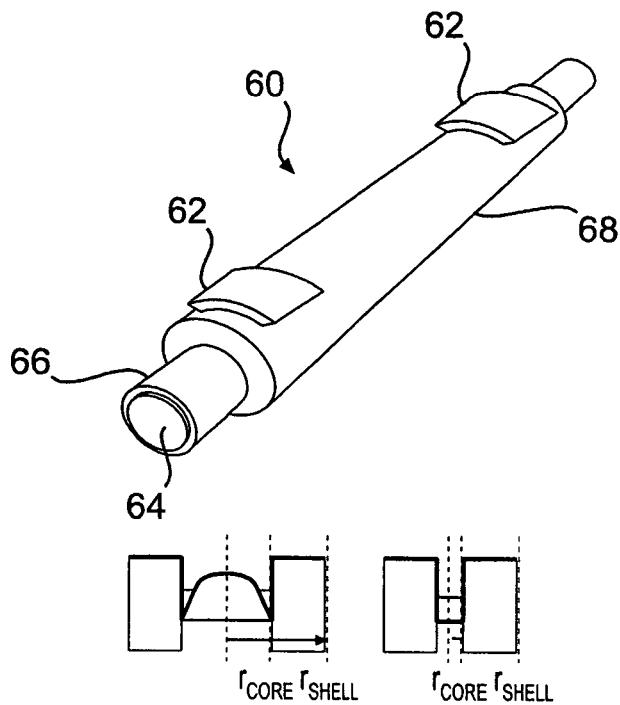
FIG. 6a shows a diagram of a first embodiment of a one-dimensional plasma device of the present invention wherein a surface within the core, or the core itself, functions as the plasmonic channel, as well as a conduction band diagram depicting the placement of the one-dimensional electron gas plasmon.

In a first embodiment of a one-dimensional (1D) device 60, shown in FIG. 6a, core 64 consists of a narrower-gap material GaAs (SiGe) (undoped) with shells 68 composed of n-type AlGaAs (Si). An inner shell will function as a spacer layer (not shown), and an outer shell as the wide-band-gap material. Ti Au Schottky contacts 62, needed for maintaining the quasi-equilibrium state of a high concentration of carriers in the channel, will be formed on the AlGaAs shells 68. The 1D plasma 66 will be formed at the interface of shell 68 and the core 64, or within core 64. The configuration of a radially symmetric, cylindrical heterojunction with the channel existing in the interior of core 64 will enable the 1D plasmon 66 to exist in a shell geometry, or extending to within all of core 64, depending on core diameter, doping levels and bias. The relevant theoretical diameter for the core or for shell thickness is that for which there is no significant deviation from the linear dispersion of the plasmon 66 as discussed above, and correspondingly no decay into single particle, or electron-hole states. Nanowires with diameters and shells on the order of a several Fermi wavelengths or an appropriate screening length (depending upon the doping level) or smaller is appropriate for the instant invention. Typically, the diameter will be smaller than 100 nm.

Figure 6B:
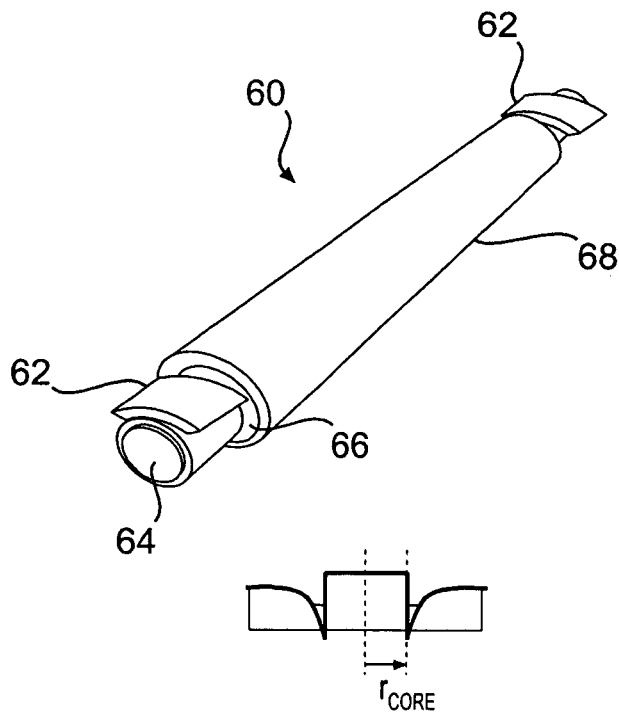
FIG. 6b shows a diagram of a second embodiment of a one-dimensional device of the present invention wherein a surface within the shell functions as the plasmonic channel, and as well as a conduction band diagram depicting the placement of the one-dimensional electron gas plasmon.

In the second device embodiment, shown in FIG. 6b, core 64 and shell 68 materials are reversed. Core 64 is composed of the wider-gap material, AlGaAs (Si) the quasi 1DEG plasmon 66 is formed within the GaAs (SiGe) shell 68 and Ti Au Schottky contact 62 is made to the nanowire core 64. In addition, devices can be fabricated in which the band-gap of the plasmonic cavity will be spatially modulated using composition modulation of the undoped $Al_xGa_{1-x}As$ in which $x=\sin(2\pi nz/L)$ where L is the length of the nanowire between the reflective ends, and z is the axis of the nanowire. The wavelength of the spatial modulation of $E_g$ in core 64 is preferably chosen to be commensurate with the plasmon wavelength of interest. For example, if it is desired to sense radiation of specifically 30 THz in energy, or a wavelength of 10 μm the value of $E_g$ within the nanowire core would be spatially modulated on this length scale. Since it is known to those skilled in the art that nanowire lengths can exceed many tens of μm and approaching 100 μm or more, the important range within the THz band may be addressed using this resonant technique involving bandgap modulation.

The quality of the nanowires can be determined using scanning and transmission electron microscopy, selected area and converging beam electron diffraction, energy dispersive X-ray spectroscopy and scanning probe microscopy.

Schottky contacts 62 are established using electron beam and/or thermal evaporation facilities. These nanowire core and shell contacts are patterned using photolithography, electron-beam lithography and focused ion beam facilities. The 1D devices 60 can be used as nanowire-based photodetectors to determine a response to visible radiation. This response is due to perturbation of the electron cloud by optical stimulus, and subsequent collection of photoinduced charge carriers at the contacts in the form of a current. The 1D devices 60 are also useful as nanowire plasma-based detectors of THz radiation. In addition to electromagnetic radiation these devices can be used as detectors of charged particle perturbations, such as those found in electron beams.

Other materials that can be used for the 1D device, in either core 64 or in the shell layers 68, include, but are not limited to, Ge, InN, InGaN, Si, InP, AlAs, InAs, AlGaN, CdSe, CdS, CdTe, PbSe, PbS, PbTe, ZnSe, ZnBeSe, ZnS, ZnBeS, GaSb, InSb, SiC, and GaN. Additionally, those materials not included above grouped as III-V, II-VI, and group IV semiconductors can be used.

The spectral response of the 1D plasma (in the geometrical form of a core or a shell, depending upon the configuration selected as shown in the FIGS. 6a and 6b) can be tuned to a selected terahertz frequency with a narrow bandwidth using one or more of the following methods.

When core 64 of the coaxial nanowire 1D device geometry includes the narrower-gap, 1D plasma 66 (electron or hole gas plasma), either throughout the core diameter, or within a selected radius-shell, one embodiment involves the introduction of periodic spatial modulation of the energy gap of core 64 such that the spatial wavelength of the modulation is commensurate with the plasmon wavelength in the solid, reinforcing the selected frequency. Secondly, the nanowire ends may be reflective so as to reinforce the cavity-like nature of the nanowire in accommodating the plasmon without dissipation in the structure. For example, core 64 may consist of a sinusoidal variation in composition between the limits of Si and $Si_xGe_{1-x}$, since the former has a larger band-gap than the alloy.

It is well known that hole mobilities are typically lower in value than electron mobilities. In 2DEG systems the formation of spatially distinct 2DEG and 2DHG may be formed within the same planar device. The 1D plasmon may be fabricated as distinct hole and electron gases within the same nanowire device by adding additional shells with appropriate dopant type and concentration. Both a hole plasmon and an electron plasmon may be introduced within different shells, or a portion of the core and a shell.

When 1D device geometry is fabricated such that the lower energy-gap plasma is within one or more of the shell layers, core 64 may be fabricated to produce spatial, periodic modulation in the free carrier concentration, thereby influencing the local charge density in the plasmon in the adjacent shell 68, leading to a reinforcement of a selected plasmon wavelength.

A 1D device 60 may be produced with a response having selected spectral characteristics (band, shape, roll-off characteristics, etc.) This will be accomplished by designing the band-gap or carrier concentration modulation such that its spatial Fourier transform, when convolved with the excitation spectrum, leads to a desired spectral response. In practice, the long lengths of the nanowires (tens of micrometers) and the nearly dissipation less plasmons (i.e. not decaying into single particle excitations) provide the basis for this enhanced feature.

Furthermore, information—essentially additional effective bandwidth—can be contained within the polarization state of electromagnetic radiation. Polarization sensitive detectors offer important additional capabilities. These detectors, on the basis of their one-dimensional nature (due to the dielectric response of a charged filament) will be sensitive to the polarization state of the electromagnetic field (here the terahertz radiation). With this innovation, arrays/assemblies of these 1D devices 60, functioning as plasmonic sensors may be used to detect and/or filter polarized terahertz radiation, as well as identify the static nature or time-dependence of the polarization state.

In addition the observation that the plasmon dispersion is altered in selected 1D devices 60 of different configuration, effective carrier concentration, diameter and bias can be obtained using low-temperature resonant Raman scattering, it may also be possible to use inelastic neutron scattering. Instrumentation facilities that consist of both visible and UV systems, with scanning probes, infrared reflectivity devices, and near field optical and confocal microscopy options can be used to obtain further measurements of the responses of 1D devices 60. These measurements can be used to probe the excitation spectrum of the confined plasmon in a more direct manner.

1D devices 60 used for the sensing of terahertz radiation can have significant impact in research and development and be used in diverse areas, including plasma fusion, electron bunch diagnostics, gas spectroscopy, mapping of current distribution in electronics and THz spintronics, for enhanced medical imaging, applications in homeland security, and chemical and biological agent detection, explosives detection, and satellite-based space imaging. The development of new platforms for high-sensitivity, fast-response, tunable detection on non-traditional substrates and in nanostructured form will be an enabling technology, opening this region of the EM spectrum to a broader range of investigation, development and application. This work is also beneficial to those involved in optical and charged particle detection methods and their applications.

Figure 7:
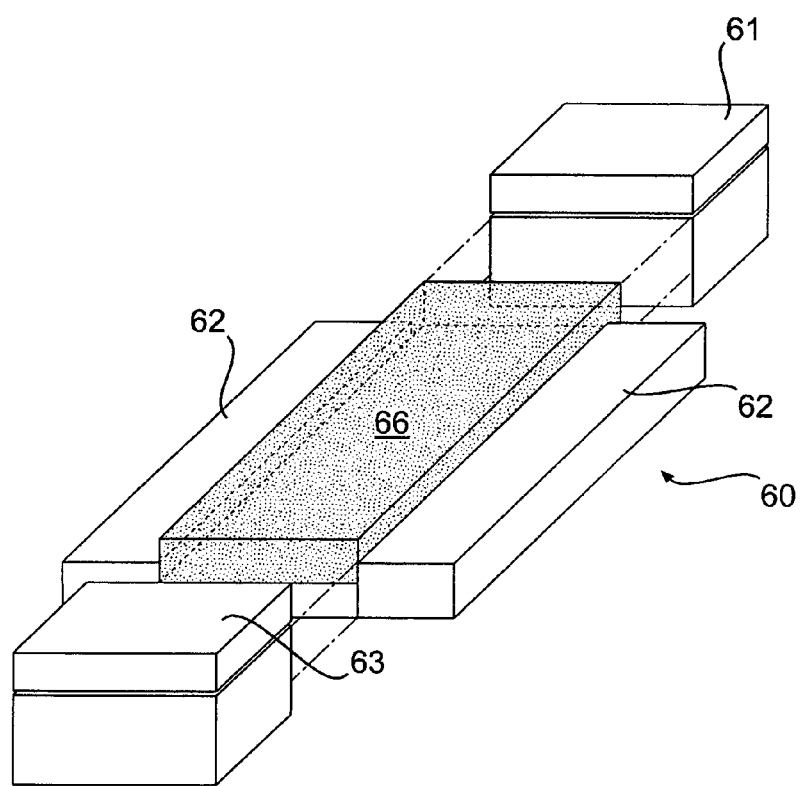
FIG. 7 shows another embodiment of a one-dimensional device that is produced by confining the two dimensional electron gas (2DEG) by exerting potential via blocking Schottky contacts to its sides in order to produce a filament of charge, i.e. a 1DEG wire.
Figure 8:
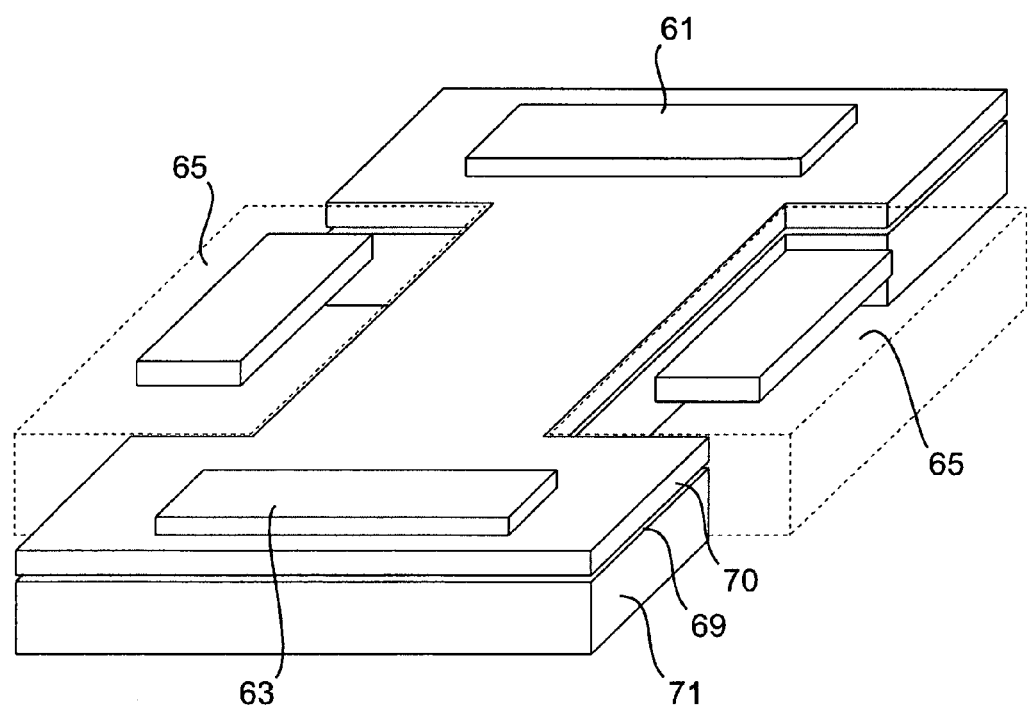
FIG. 8 shows yet another embodiment of a one dimensional device in which the two dimensional electron gas (2DEG) is confined from the sides by p-type doped side gates.

The 1D device that is illustrated in FIGS. 6a and 6b and explained above, is created using a bottom-up approach, however it can also be accomplished by using a top down approach that is shown in FIGS. 7 and 8. In these embodiments a two-dimensional electron gas 69 is produced by a layer structure similar to that shown in FIG. 3c by using drain 61 and source 63 contacts. This 2DEG 69 is electrostatically confined to one-dimension by side, or top gates 62 and is used to form 1D device 60. FIG. 7 shows side gates formed by etching and depositing Schottky contacts 62 to the sides of a 2DEG in order to produce a 1 DEG 66. FIG. 8 shows the same structure but with the side gates 65 produced by a p-type doped semiconductor. The p-doping can be done by ion implantation. The device of FIG. 8 includes a wide gap 70 and a narrow gap 71. Presently, Focused Ion Beam (FIB) instruments are capable of achieving the necessary resolution for this purpose. Re-growth techniques such as Metal Organic Chemical Vapor Deposition (MOCVD) can also be used to grow the highly doped p-type side gates. The contacts noted as source 63 and drain 61 in FIGS. 7 and 8 can be either Schottky or ohmic and play the same role as the contacts placed at the end of nanowires. An advantage of the side-gates 65 is that they provide a mechanism for controlling the density of a 1D charge, thus being able to tune the frequency of detection.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A detector for detecting electromagnetic radiation and charged particles comprising:
   an inner material;
   an outer material surrounding said inner material;
   a one-dimensional plasma in the detector having a confined charge at quasi-equilibrium,
   Schottky contacts associated with at least one of said inner and outer materials, wherein said Schottky contacts are located at ends of the confined charge;
   wherein the detector is tuned to a resonant frequency by modulating the composition and the band-gap along a detector length and
   wherein said one-dimensional plasma forms a collective response.

2. The detector of claim 1, wherein said electromagnetic radiation is terahertz radiation.

3. The detector of claim 1, wherein said resonant frequency is adjusted by controlling charge carrier density.

4. The detector of claim 3, wherein said charge carrier density is further adjusted by doping of said inner or outer material.

5. The detector of claim 3, wherein said one-dimensional plasma comprises at least one energy gap.

6. The detector of claim 1, further comprising an additional one-dimensional plasma confined in the detector.

7. The detector of claim 6, wherein the collective charge carrier behavior of said additional one-dimensional plasma is different than the collective charge carrier behavior of said one-dimensional plasma.

8. A detector for detecting electromagnetic radiation and charged particles comprising:
   a core comprised of a first material;
   a shell comprised of a second material;
   reflective ends;
   a one-dimensional plasma having a confined charge at quasi-equilibrium in the shell;
   Schottky contacts directly contacting said core;
   wherein an energy gap of the core is periodically spatially modulated to tune to a resonant frequency; and
   wherein said first material is a wider-gap material than said second material.

9. A detector for detecting electromagnetic radiation and charged particles comprising:
   an inner material;
   an outer material surrounding said inner material;
   a one-dimensional plasma in the detector having a confined charge, wherein said one-dimensional plasma collectively carries negative or positive charge;
   Schottky contacts associated with at least one of said inner and outer materials wherein said Schottky contacts are located at ends of the confined charge; and
   wherein the core has a sinusoidal variation in composition to adjust said resonant frequency by controlling charge carrier density.

* * * * *